(12) United States Patent
Atia et al.

(10) Patent No.: US 7,061,618 B2
(45) Date of Patent: Jun. 13, 2006

(54) INTEGRATED SPECTROSCOPY SYSTEM

(75) Inventors: Walid A. Atia, Lexington, MA (US); Dale C. Flanders, Lexington, MA (US); Petros Kotidis, Framingham, MA (US); Mark E. Kuznetsov, Lexington, MA (US)

(73) Assignee: Axsun Technologies, Inc., Billerica, MA (US)

( * ) Notice: Subject to any disclaimer, the term of this patent is extended or adjusted under 35 U.S.C. 154(b) by 249 days.

(21) Appl. No.: 10/688,690

(22) Filed: Oct. 17, 2003

(65) Prior Publication Data

US 2005/0083533 A1    Apr. 21, 2005

(51) Int. Cl.
*G01B 9/02* (2006.01)

(52) U.S. Cl. ..................... 356/454; 356/519
(58) Field of Classification Search ............... 356/480, 356/451, 519, 454
See application file for complete search history.

(56) References Cited

U.S. PATENT DOCUMENTS

| 5,475,221 | A | 12/1995 | Wang | |
|---|---|---|---|---|
| 5,818,586 | A * | 10/1998 | Lehto et al. | 356/454 |
| 6,381,022 | B1 * | 4/2002 | Zavracky | 356/454 |
| 6,407,376 | B1 | 6/2002 | Korn et al. | |

FOREIGN PATENT DOCUMENTS

| DE | 41 22 925 A1 | 1/1993 |
|---|---|---|
| EP | 0 709 659 A2 | 5/1996 |

OTHER PUBLICATIONS

Brochure, "Agilent 83437A Broadband Light Source and Agilent 83438A Erbium ASE Source, Production Overview," Agilent Technologies, 1996, 2002.
Vakhshoori, D. et al., "Raman Amplification Using High-Power Incoherent Semiconductor Pump Sources," Ahara Corporation, MA, 2003.
Krawczyk, S. K. et al., "GaN and Related Compunds for MEMS and MOEMS," Aromagraph DC 2000 System, vol. 51, No. 8, 1999, pp. 623-625.

* cited by examiner

*Primary Examiner*—Gregory Toatley
*Assistant Examiner*—Marissa J Detschel
(74) *Attorney, Agent, or Firm*—Houston Eliseeva LLP

(57) ABSTRACT

Integrated spectroscopy systems are disclosed. In some examples, integrated tunable detectors, using one or multiple Fabry-Perot tunable filters, are provided. Other examples use integrated tunable sources. The tunable source combines one or multiple diodes, such as superluminescent light emitting diodes (SLED), and a Fabry Perot tunable filter or etalon. The advantages associated with the use of the tunable etalon are that it can be small, relatively low power consumption device. For example, newer microelectrical mechanical system (MEMS) implementations of these devices make them the size of a chip. This increases their robustness and also their performance. In some examples, an isolator, amplifier, and/or reference system is further provided integrated.

27 Claims, 18 Drawing Sheets

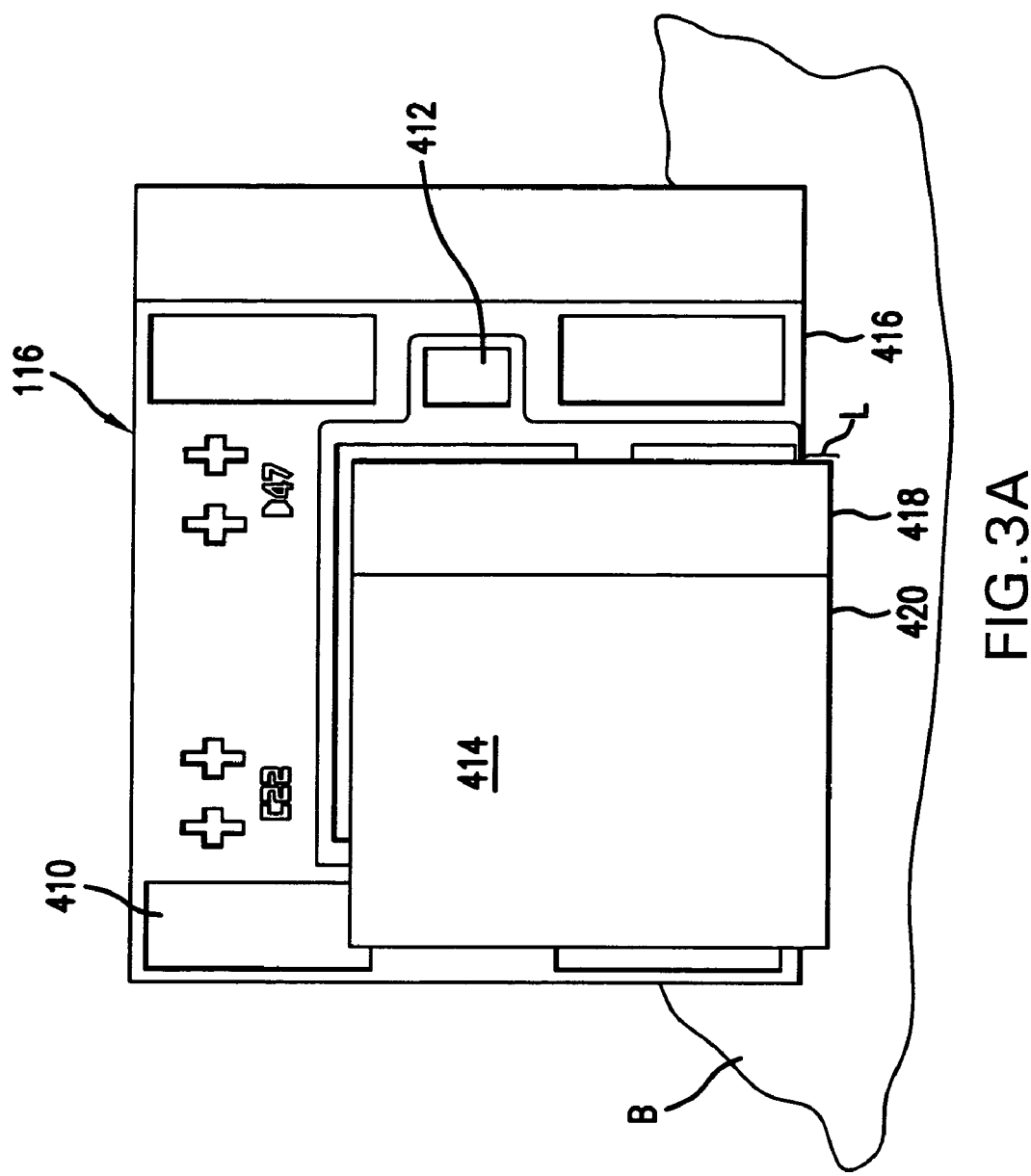

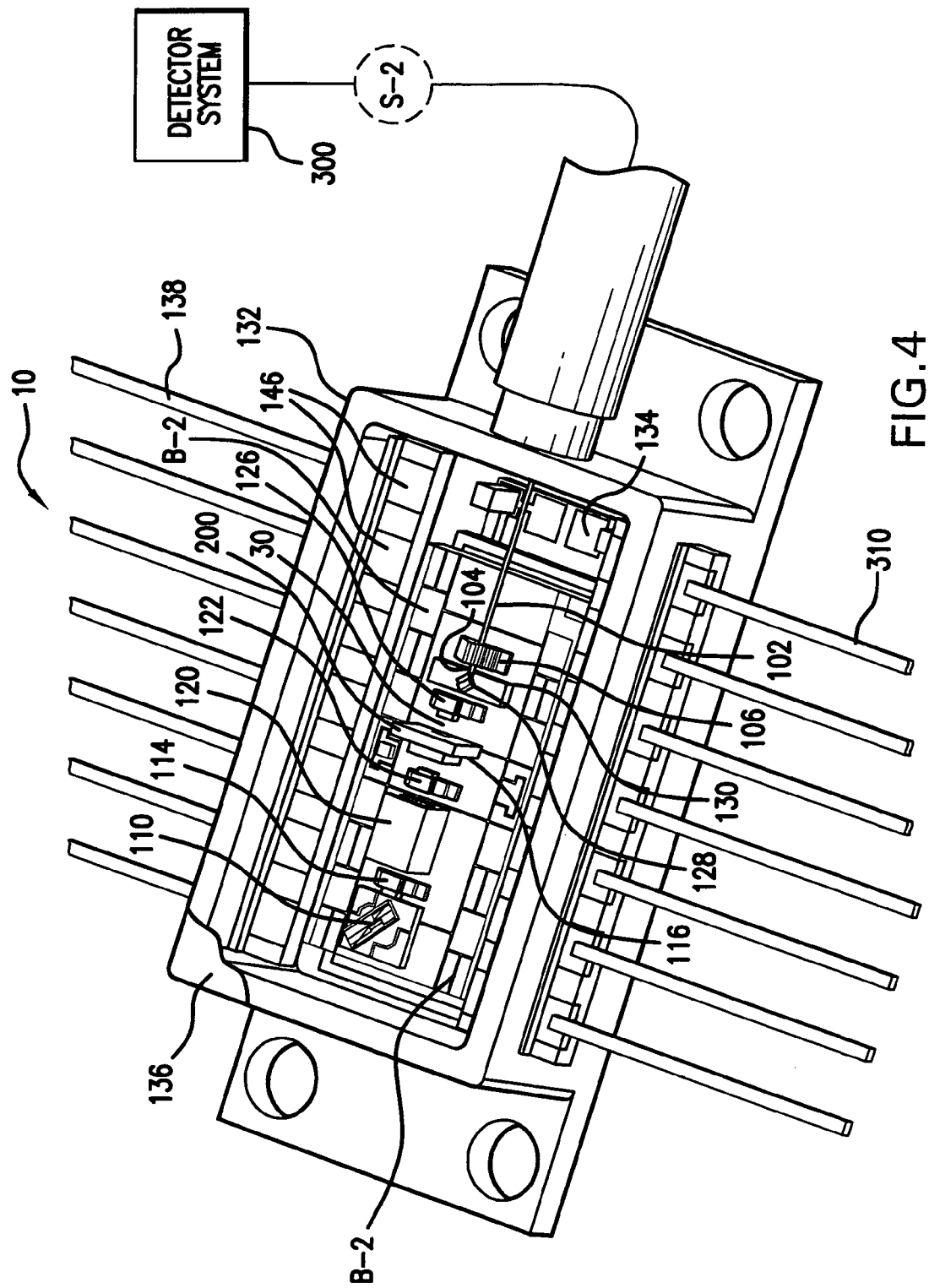

INTEGRATED SPECTROSCOPY SYSTEM

BACKGROUND OF THE INVENTION

Minimally, optical spectroscopy systems typically comprise a source for illuminating a target, such as a material sample, and a detector for detecting the light from the target. Further, some mechanism is required that enables the resolution of the spectrum of the light from target. This functionality is typically provided by a spectrally dispersive element.

One strategy uses a combination of a broadband source, detector array, and grating dispersive element. The broadband source illuminates the target in the spectral scan band, and the signal from the target is spatially dispersed using the grating, and then detected by an array of detectors.

The use of the grating, however, requires that the spectroscopy system designer make tradeoffs. In order to increase the spectral resolution of these systems, aperturing has to be applied to the light provided to the grating. As more spectral resolution is required, more light is required to be rejected by the narrowing spatial filter. This problem makes this strategy inappropriate for applications requiring a high degree of spectral precision combined with sensitivity.

Another approach is to use a tunable narrowband source and a simple detector. A typical approach relies on a tunable laser, which is scanned over the scan band. By monitoring the magnitude of the tunable laser's signal at the detector, the spectrum of the sample is resolved. These systems have typically been complex and often had limited wavelength scanning ranges, however.

Still another approach uses light emitting diodes (LEDs) and an acousto-optic modulator (AOM) tunable filter. One specific example combines multiple light emitting diodes (LEDs) in an array, each LED operating at a different wavelength. This yields a relatively uniform spectrum over a relatively large scan band. The light from the diodes is then sent through the AOM tunable filter, in order to create the tunable optical signal.

The advantage of this system is the use of the robust LED array. This provides advantages over previous systems that used other broadband sources, such as incandescent lamps, which had limited operating lifetimes and high power consumption.

While representing an advance over the previous technology, the disadvantages associated with this prior art system were related to the use of the AOMs, which are relatively large devices with concomitantly large power consumptions. Moreover, AOMs can also be highly temperature sensitive and prone to resonances that distort or alter the spectral behavior, since they combine a crystal with a radio frequency source, which establishes the standing wave in the crystal material to effect the spectral filtering.

Grating-based spectrometers also tend to be large devices. The device packages must accommodate the spatially dispersed signal from the sample. Further, the interface between the grating and the detector array must also be highly mechanically stable. Moreover, these grating based systems can be expensive because of costs associated with the detector arrays or slow if mechanical scanning of the detector or grating is used.

SUMMARY OF THE INVENTION

The drawbacks associated with the prior art spectrometers arise from the large size of the devices combined with the high cost to manufacture these devices combined with poor mechanical stability. These factors limit the deployment of spectrometers to applications that can justify the investment required to purchase these devices and further accommodate their physical size.

Accordingly, the present invention is directed to an integrated spectrometer system. Specifically, it is directed to the integration of a tunable Fabry-Perot system with a source system and/or detector system. The use of the Fabry-Perot filter system allows for a high performance, low cost device. The integration of the filter system with the source system and/or detector system results in a device with a small footprint. Further, in the preferred embodiment, the filter system is based on microelectromechancial systems (MEMS), which yield a highly mechanically robust system.

In general, according to one aspect, the invention features a spectroscopy system. The system comprises a source system for generating light to illuminate a target, such as a fiber grating or a material sample. A tunable Fabry-Perot filter system is provided for filtering light generated by the source. A detector system is provided for detecting light filtered by the tunable filter from the target. According to the invention, at least two of the source system, tunable Fabry-Perot filter system, and the detector system are integrated together.

Specifically, in one embodiment, the source system and tunable Fabry-Perot system are integrated together on a common substrate, such as an optical bench, also sometimes called a submount. In another embodiment, the tunable Fabry-Perot filter system and the detector system are integrated together on a common substrate, such as an optical bench. Finally, in still another implementation, all three of the source system, tunable Fabry-Perot filter system, and the detector system are integrated together on a common bench, and possibly even in a common hermetic package.

Temperature control is preferably provided for the system. Currently this is provided by a heater, which holds the temperature of the system above an ambient temperature, or a thermoelectric cooler. For example, the thermoelectric cooler is located between the bench and the package to control the temperature of the source system, tunable Fabry-Perot filter system, and/or the detector system. As a result, a single cooler is used to control the temperature of the filter and SLED chip, lowering power consumption, decreasing size, while increasing stability.

In the preferred embodiment, the source system comprises a broadband source. This can be implemented using multiple, spectrally multiplexed diode chips. Preferably, superluminescent light-emitting diodes (SLEDs) are used. These devices have a number of advantages relative to other sources, such incandescent sources. Specifically, they have better spectral brightness, longer operating lifetimes, and a smaller form factor.

In order to increase the spectral accuracy of the system, a tap can also be used to direct a part of the tunable signal to a detector. A spectral reference, such as a fixed etalon with multiple spectral transmission peaks is placed between the detector and the tap, in order to create a fringe pattern on the detector during the scan, thereby enabling monitoring of the wavelength of the tunable signal. An optical power tap can also be included to monitor the real time emitted optical power during the scan.

The tunable Fabry-Perot filter system comprises single or multiple filters. In one example, multiple serial filters are used. In another embodiment, multiple parallel filters are used.

In still further embodiments, multiple detectors can be used. These detectors can be responsive to different wavelengths or a calibration signal.

In the preferred embodiment, in order to make the system small, compact and highly robust, a micro-electro-mechanical system (MEMS) Fabry-Perot tunable filter is used. These devices can achieve high spectral resolutions in a very small footprint.

Finally, in the preferred embodiment, isolation is provided between the source system and the tunable Fabry-Perot filter system. This prevents back reflections from the filter into the source system that can disturb the operation of the source system. In one example, an isolator is installed on the optical bench between the SLED and the tunable filter. A quarter wave plate can also be used. This rotates the polarization of the returning light so that it is not amplified by the highly polarization anisotropic SLED gain medium. In another embodiment, the isolation is provided on the bench, with the tunable Fabry-Perot filter system and the detector system.

The present invention is also directed to an integrated tunable source that combines a broadband source and a tunable filter, such as a tunable Fabry-Perot filter, although other tunable filters could be used in this configuration. Applications for this device extend beyond spectroscopy.

Between the tunable filter and the light source, isolation is preferably provided. This stops back reflections from the tunable filter into the diode, which could impact its performance. Isolation can be achieved using a number of techniques. In one embodiment, a discrete isolator is used. In another embodiment, when a SLED is used as the source, a quarterwave plate is used between the SLED chip and the filter. Finally, a flat-flat cavity Fabry-Perot tunable filter is used in still another embodiment, with isolation being accomplished by tilting the filter relative to the SLED.

A variety of other light sources can be used, including LEDs, doped fiber or waveguide amplified spontaneous emission sources, and thermal sources.

According to still another aspect, the invention features a high power tunable source. This addresses one of the primary drawbacks associated with the use of a broadband source and tunable filter configuration, namely their usually low output power. Specifically, an optical amplifier is further added in order to increase the power of the tunable signal. As a result, power levels comparable to those attainable with tunable lasers can be achieved in this configuration.

In a typical implementation, the amplifier is a semiconductor optical amplifier (SOA). In other examples, various types of fiber amplifiers are used, however.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

FIG. 3A is a perspective view of the MEMS Fabry Perot tunable filter, used in embodiments of the present invention, which is compatible with tombstone mounting on the optical bench;

FIG. 4 is a perspective view showing an amplified tunable source, according to the present invention, in a hermetic package;

DETAILED DESCRIPTION OF THE PREFERRED EMBODIMENTS

Figure 1A:
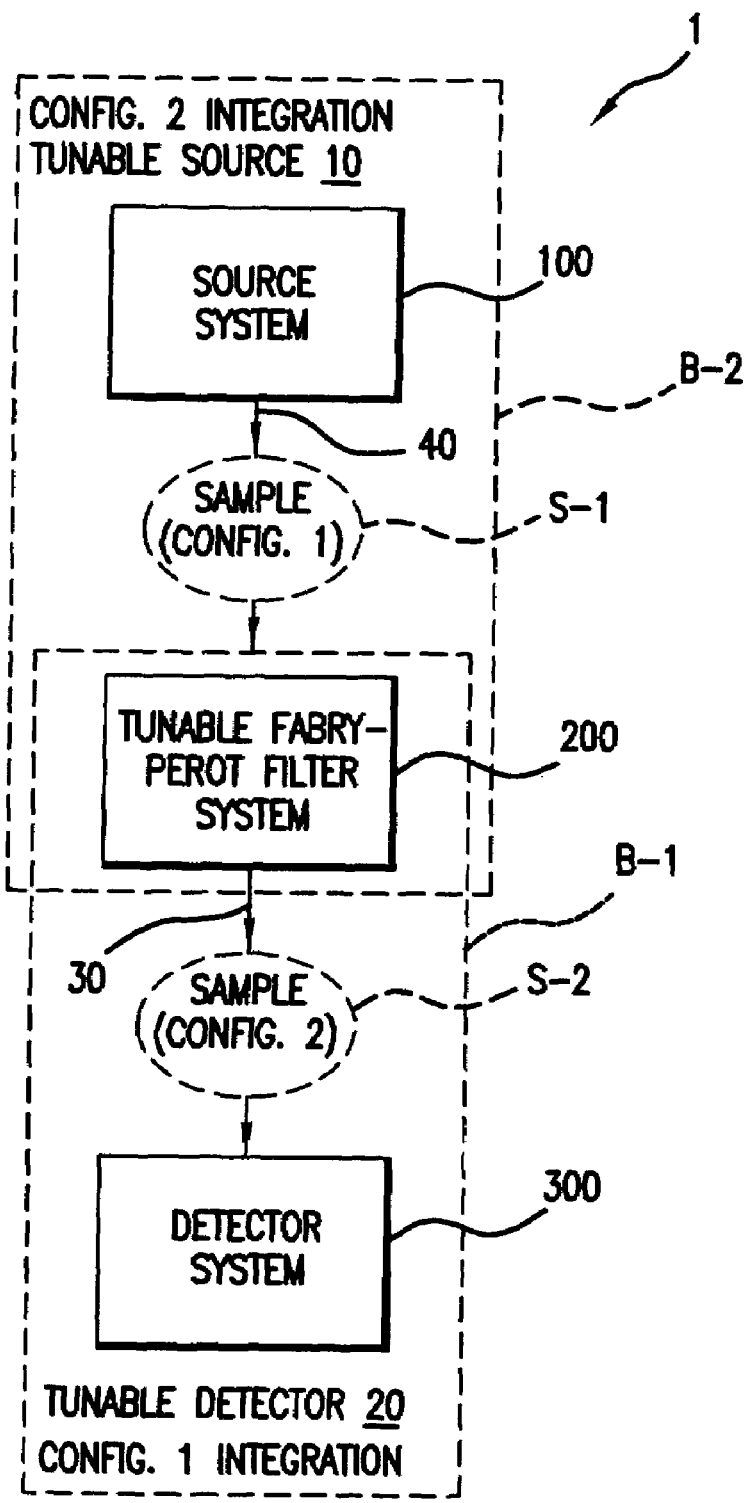
FIGS. 1A and 1B illustrate embodiments of the integrated spectroscopy system according to the present invention.
Figure 1B:
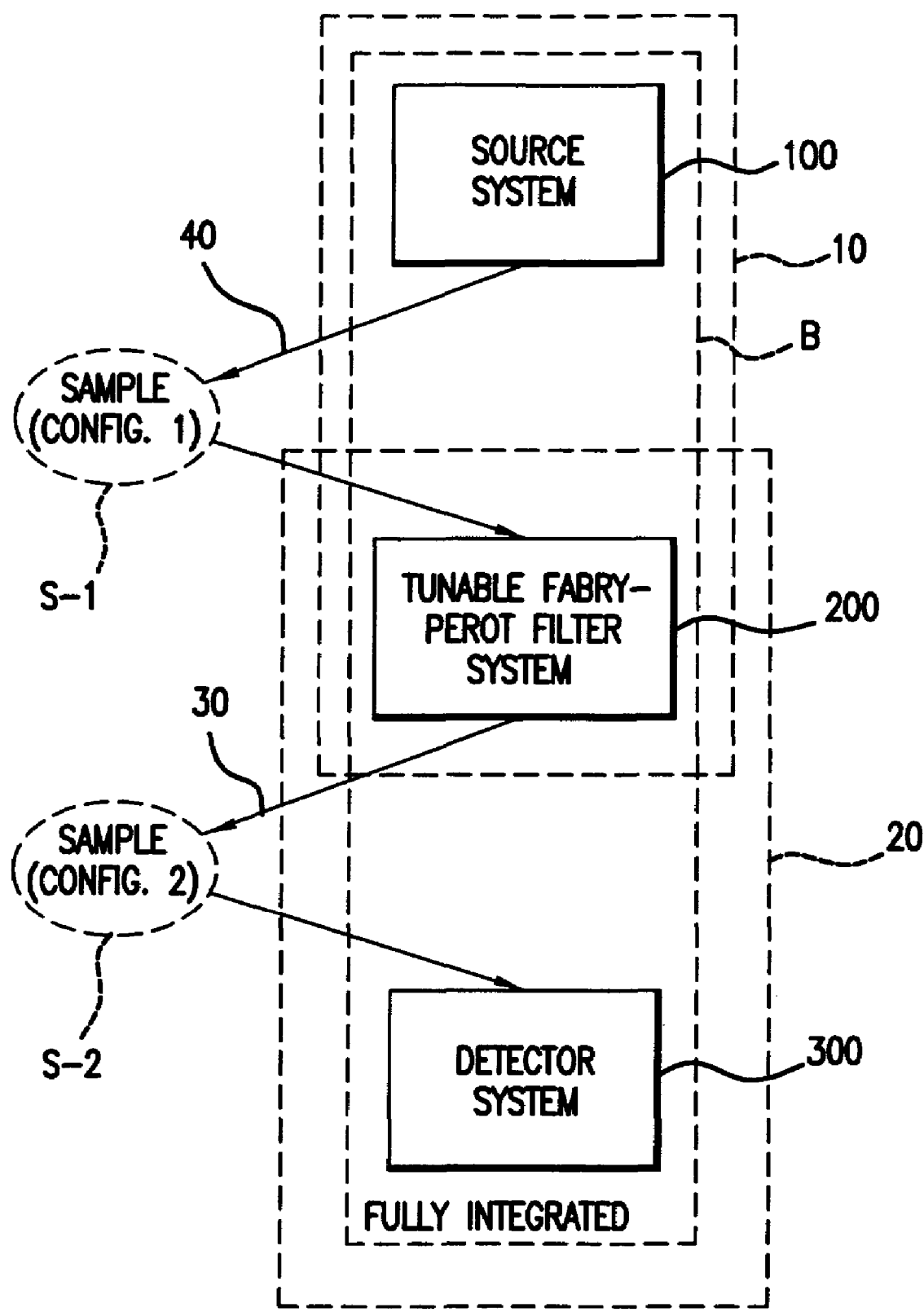

FIGS. 1A and 1B illustrate an integrated spectroscopy system 1, which has been constructed according to the principles of the present invention.

Specifically, FIG. 1A shows two alternative integration configurations.

According to configuration 1, a source system 100 is provided. This is a broadband source, which generates light 40 for illuminating a target, such as sample S-1 or a fiber grating, for example. This target selectively absorbs and/or scatters the light from the source system 100. The transmitted light is then received by a tunable Fabry-Perot filter system 200. This functions as a narrow band tunable spectral filter. It tunes its passband over the scan band within the spectral band of the source system 100. As a result, it resolves the spectrum of the target S-1 into a time response. This time-resolved signal is then detected by detector system 300.

According to the integration provided by this configuration 1, the tunable Fabry-Perot filter system 200 and the detector system 300 are integrated together. Specifically, in the preferred embodiment, the tunable Fabry-Perot filter system 200 and the detector system 300 are installed on a common bench B-1. Moreover, in the current embodiment, the tunable Fabry-Perot filter system 200 and the detector system 300 are integrated together on the common bench B-1 in a common hermetic package.

The integration of the Fabry-Perot filter system 200, with the detector system 300 on the common bench B-1, yields the tunable detector 20 which is characteristic of the configuration 1 integration.

FIG. 1A also illustrates a second configuration, configuration 2 integration. In this second configuration, the source system 100 and the tunable Fabry-Perot system 200 are integrated together. In the preferred embodiment, they are installed together on a common bench B-2. Further, in the current implementation, the source system 100 and the tunable Fabry-Perot filter system are integrated together on the common bench B-2 and installed in a common hermetic package to yield a tunable source 10. This tunable source 10 generates a tunable signal 30, which is used to illuminate a target, located in this second configuration at position S-2. The target either scatters or absorbs spectral components of the tunable signal as it is scanned across the scan band. This allows the detector system 300 to resolve the time varying signal as the spectral response of the target S-2.

FIG. 1B illustrates a fully integrated system according to still another embodiment. Here, the source system 100, the tunable Fabry-Perot filter system 200, and the detector system 300 are integrated together. Specifically, in the preferred embodiment, they are integrated together and installed on a common bench B. This bench B is preferably located in a hermetic package.

Depending on whether the tunable source system 100, the Fabry-Perot filter system 200, and detector system 300, are combined as a tunable source 10 or tunable detector 20, the target is located either in position S-1 or S-2. Specifically, in the implementation of a tunable source 10 with the source system 100 and the tunable Fabry-Perot filter system 200 functioning to create a tunable signal, the tunable signal 30 is coupled outside of the hermetic package and off of the bench B to the target S-2, in the case of configuration 2. Alternatively, if the tunable Fabry-Perot filter system 200 and the detector system 300 function to yield the tunable detector 20, then the broadband signal 40 from the source system 100 is coupled off of the bench and the outside of the hermetic package to the target S-1 in the case of the first configuration.

Figure 2:
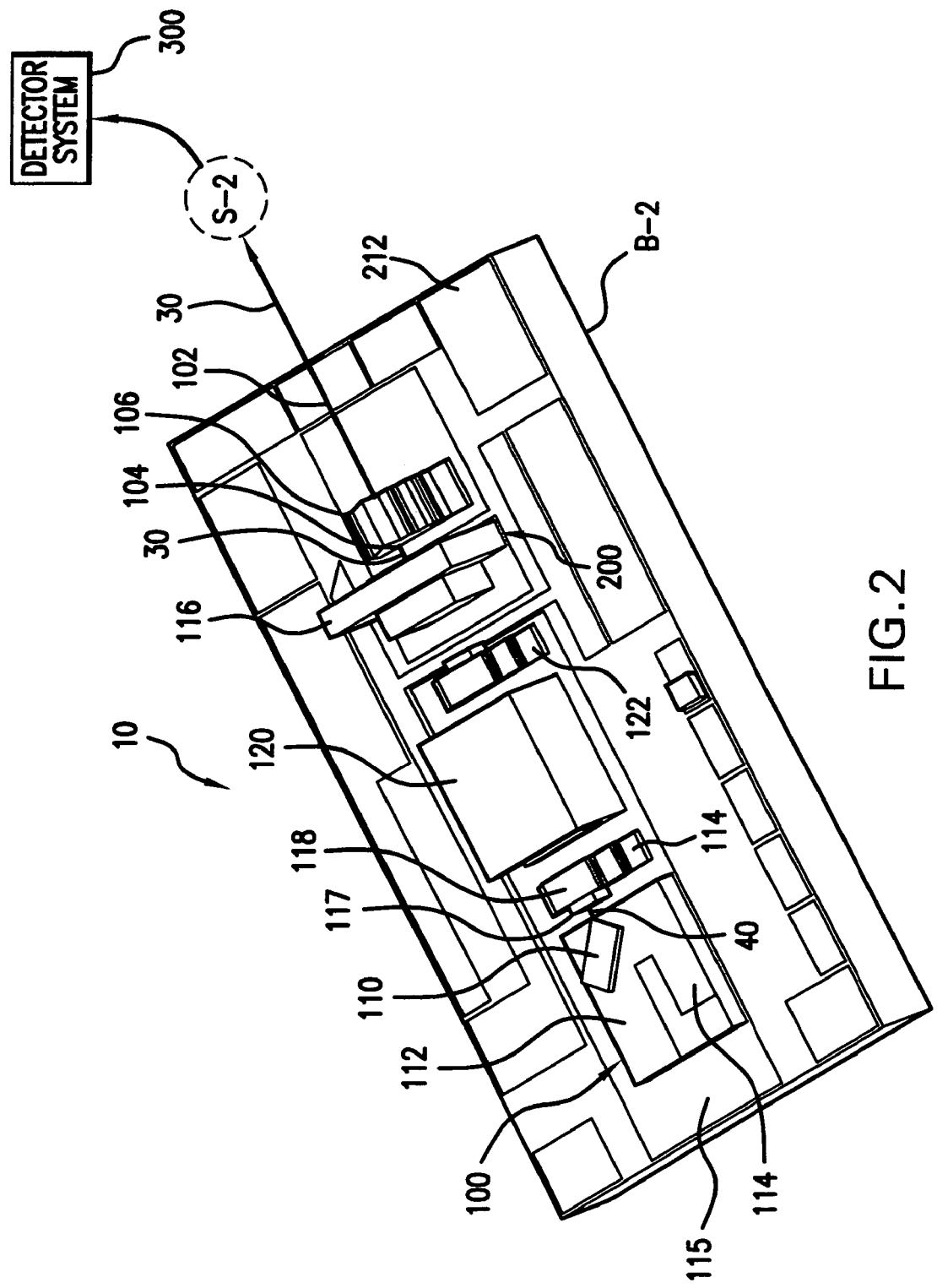
FIG. 2 is a perspective view showing a tunable source, according to the present invention, and including a detector system for detecting the tunable signal from the sample.

FIG. 2 illustrates a first embodiment of the tunable source 10. Specifically, in this embodiment, the bench B-2 holds the tunable Fabry-Perot filter system 200 and the source system 100 on a common planar surface. The generated tunable signal 30 is coupled off of the bench B-2 by an optical fiber 102. In the preferred embodiment, this optical fiber 102 is a single transverse mode fiber. This has advantages in that it renders the tunable signal 30 very stable, even in the event of mechanical shock to the single mode fiber 102.

The source system 100 is implemented using, in this embodiment, a superluminescent light emitting diode (SLED) 110. The diode 110 is installed on a submount 112. The submount 112 is, in turn, installed on the bench B-2. In the preferred embodiment, the SLED chip 110 is solder bonded to the submount 112, which further includes metallizations 114 to facilitate wire bonding to provide electrical power to the SLED chip 110. Further, the submount 112 is solder bonded to the bench B-2, which in turn, has metallizations 115 to enable formation of the solder bonds.

These SLEDs are relatively new, commercially-available devices and are sold by Covega Corporation, for example, (product numbers SLED 1003, 1005, 1006). These devices are currently available in wavelength ranges from 1,200 nanometers (nm) to 1,700 nm from a variety of vendors. They are waveguide chip devices with long gain mediums similar to semiconductor optical amplifiers. An important characteristic is their high spectral brightness.

The broadband signal 40 that is generated by the SLED chip is collimated by a first lens component 114. This lens component 114 comprises a lens substrate 117, which is mounted onto a deformable mounting structure 118. The deformable mounting structure is preferably as those structures described in U.S. Pat. No. 6,559,464 B1 to Flanders, et al., which is incorporated herein in its entirety by this reference. The alignment structure system allows for post installation alignment by mechanical deformation of the mounting structure 118 of the lens substrate 117.

The collimated light from the first lens component 114 in the preferred embodiment is coupled through an isolation system, such as an isolator 120 or quarterwave plate. The beam from the isolator is then collimated by a second lens element 122 and coupled into the Fabry-Perot tunable filter system 200. The isolator system prevents all back reflections or back reflections that have a polarization that is aligned with the gain polarization of the SLED chip 110. These reflections arise from the Fabry-Perot filter system 200. This isolation promotes the stability in the operation of the SLED chip 110.

In the preferred embodiment, the tunable filter system 200 is implemented as a MEMS tunable Fabry-Perot filter 116. This allows for single transverse mode spectral filtering of the broadband light 40 from the SLED chip 110, yielding the tunable signal 30. Tunable signal 30 is coupled into the endface 104 of the single mode optical fiber 102. In the current embodiment, the endface 104 of the optical fiber 102 is held in alignment with the MEMS tunable filter 116, via a fiber mounting structure 106. Again, this allows for post installation alignment of the fiber endface 104 to maximize coupling of the tunable signal 30, into the single mode fiber 102. The fiber 102 transmits the tunable signal 30 to target S-2 and then, the response is detected by detector system 300.

Depending on the embodiment, the Fabry-Perot filter 116 has either a curved-flat cavity or a flat-flat cavity. The curved flat cavity increases angular tolerance between the two mirrors of the Fabry-Perot filter. The flat-flat cavity provides better single mode operation. Moreover, there is the option to avoid the necessity for discrete isolators or waveplates by angle isolating the filter for the source system 100.

FIG. 3A is a close up view of the tunable filter 116. The tunable filter 116 comprises a MEMS die 410. This has a number of wire bond locations 412 for making electrical connection to the MEMS die 410. A MEMS die 410 provides the moveable mirror portion or component of the tunable filter. A fixed mirror portion or component 414 is bonded to the MEMS die 410 in order to define the Fabry Perot cavity. In one embodiment, the fixed mirror component provides the flat mirror and the MEMS die 410 provides the curved mirror.

In the preferred embodiment, the tunable filter 116 is "tombstone" mounted onto the bench B, B-1, B-2. Specifically, the fixed mirror substrate 414 extends down below the bottom of the MEMS die 416 by a distance L. Specifically, the fixed mirror substrate has a bottom surface 418 that serves as a foot that is bonded to the bench. Preferably, a layer of solder 420 is used to attach the fixed mirror substrate 414 to the bench B. In the preferred embodiment, the distance L is approximately 1–10 micrometers.

Figure 3B:
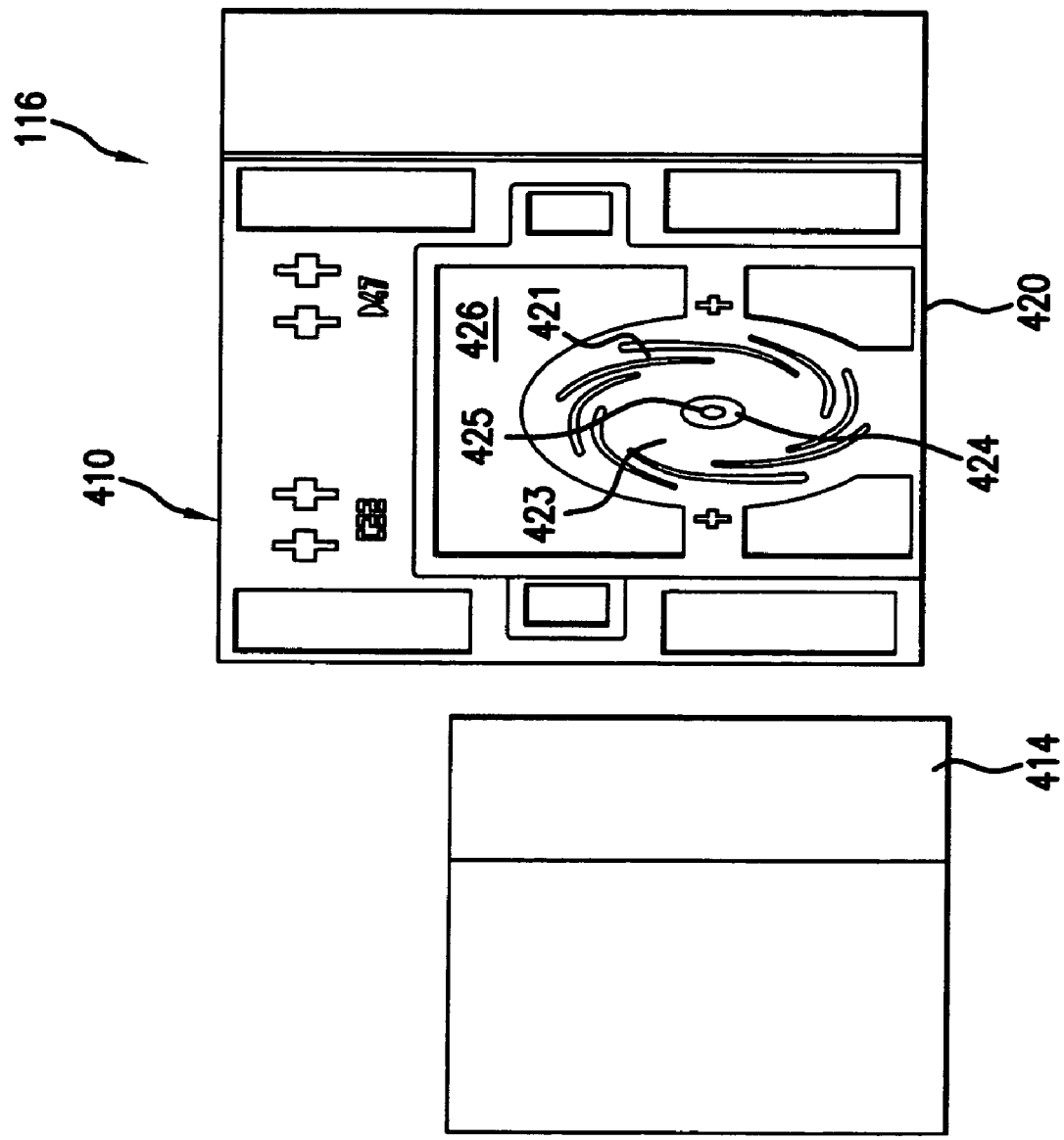
FIG. 3B is an exploded view of the inventive Fabry Perot tunable filter.

FIG. 3B is an exploded view of the tunable filter 116. This shows the fixed mirror substrate 414 disconnected from the MEMS die 410. Flexures 421 define a MEMS membrane 423. The deflectable membrane 423 holds the mirror layer 424 of the tunable mirror and covers a depression 425 formed in the membrane 423 that forms the curved mirror of one embodiment. Metallization pads 426 are provided on the MEMS die 410 in order to solder attach the fixed mirror substrate 414 to the MEMS die 410.

The general construction of this tunable filter is described in, for example, U.S. patent application Ser. No. 09/734,420, filed on Dec. 11, 2000 (now Publication No. U.S. 2002-0018385). This application is incorporated herein, in its entirety by this reference., FIG. 4 illustrates another embodiment of the tunable source 10. In this embodiment, the broadband signal generated by the SLED chip 110 is again coupled through a first lens component 114 to an isolator 120. A second lens component 122 is further provided for coupling the broadband signal into the filter 116 of the Fabry-Perot filter system 200.

Then, a third lens component 126 is provided to couple the tunable optical signal 30 into a semiconductor optical amplifier 128. In the preferred embodiment, this semiconductor optical amplifier chip 128 is installed on an amplifier sub-mount 130, which is installed on the bench B-2. The amplified tunable optical signal generated by the semiconductor optical amplifier chip 128 is then coupled into the endface 104 of the optical fiber 102 to be coupled out of the hermetic package 132. This allows the tunable signal 30 to be coupled, in an amplified state, to the target S-2 followed by detection by the detector system 300.

In some other embodiments additional isolators are located between the fiber endface 104 and the amplifier chip 128 and between the amplifier chip 128 and the third lens component 126.

In the preferred embodiment, the hermetic package 132 is a standard telecommunications hermetic package. Specifically, it comprises a standard butterfly package.

The lid 136 is shown cut away to illustrate the internal components. Further, the optical bench B-2 is preferably installed on a thermoelectric cooler 134, which enables a controlled environmental temperature to stabilize the operation of the SLED chip 110 and the tunable Fabry-Perot filter system 200.

Electrical leads 138 are further provided to transmit electrical signals to the pads 146 on the inside of the hermetic package 132. Wire bond are made between pads 146 and the active components such as the SLED chip 110, MEMS tunable filter 116, and SOA 128.

The FIG. 4 embodiment has the advantage that the tunable signal 30 received from the tunable Fabry-Perot filter system 200 is amplified to further increase the dynamic range and the signal-to-noise ratio of the spectroscopy system.

Figure 5:
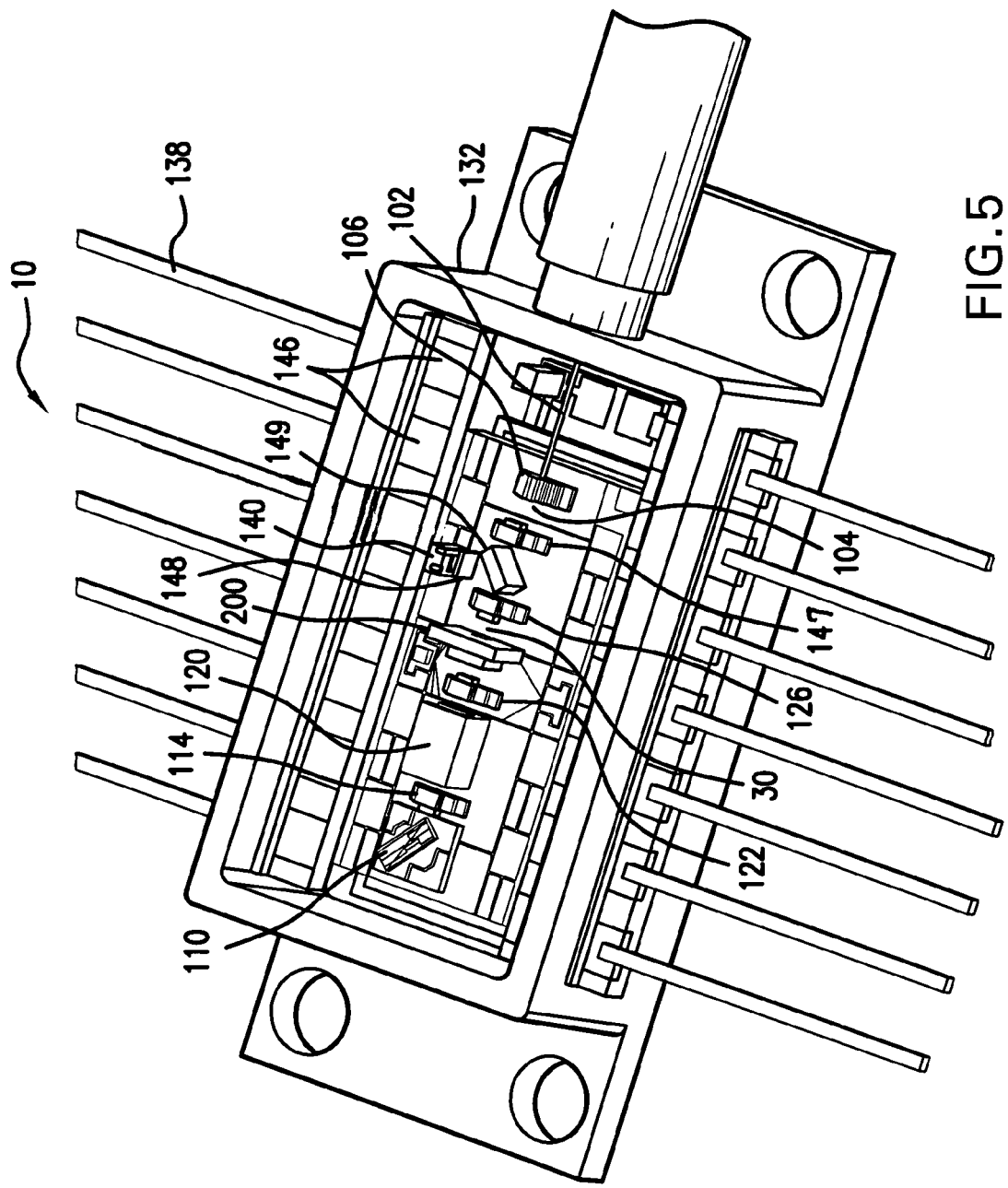
FIG. 5 is a perspective view showing a reference detector embodiment of a tunable source, according to the present invention, in a hermetic package.

In the embodiment of FIG. 5, the tunable source 10 also combines a SLED chip 110, a first lens component 114, isolator 120, and a second lens component 122. This launches the broadband signal 40 from the SLED chip into the tunable filter system 200. A third lens component 126 is further provided. This collimates the beam. A splitter, however, comprising a partially reflective substrate 149, provides a portion of the tunable signal 30 to a detector 140.

This detector 140 can be used to monitor the magnitude or power in the tunable signal 30. In another embodiment, a reference substrate 148 is installed between the detector 140 and the tap 149. This reference substrate 148 provides stable spectral features. In one embodiment, this is provided by a fixed etalon substrate. A controller monitoring the output of the detector 140 compares the tunable signal to the spectral features of the reference substrate 148 to thereby resolve the instantaneous wavelength of the tunable signal 30.

In still other embodiments, instead of a reference substrate, a gas cell is used as the spectral reference for calibrating the scan of the tunable filter 116. Also two splitters can be included to provide simultaneous spectral and power references.

The tunable signal, which is not coupled to the detector 140 by the tap 149 is launched by a fourth lens component 147 into the fiber endface 104 of the optical fiber 102.

Figure 6:
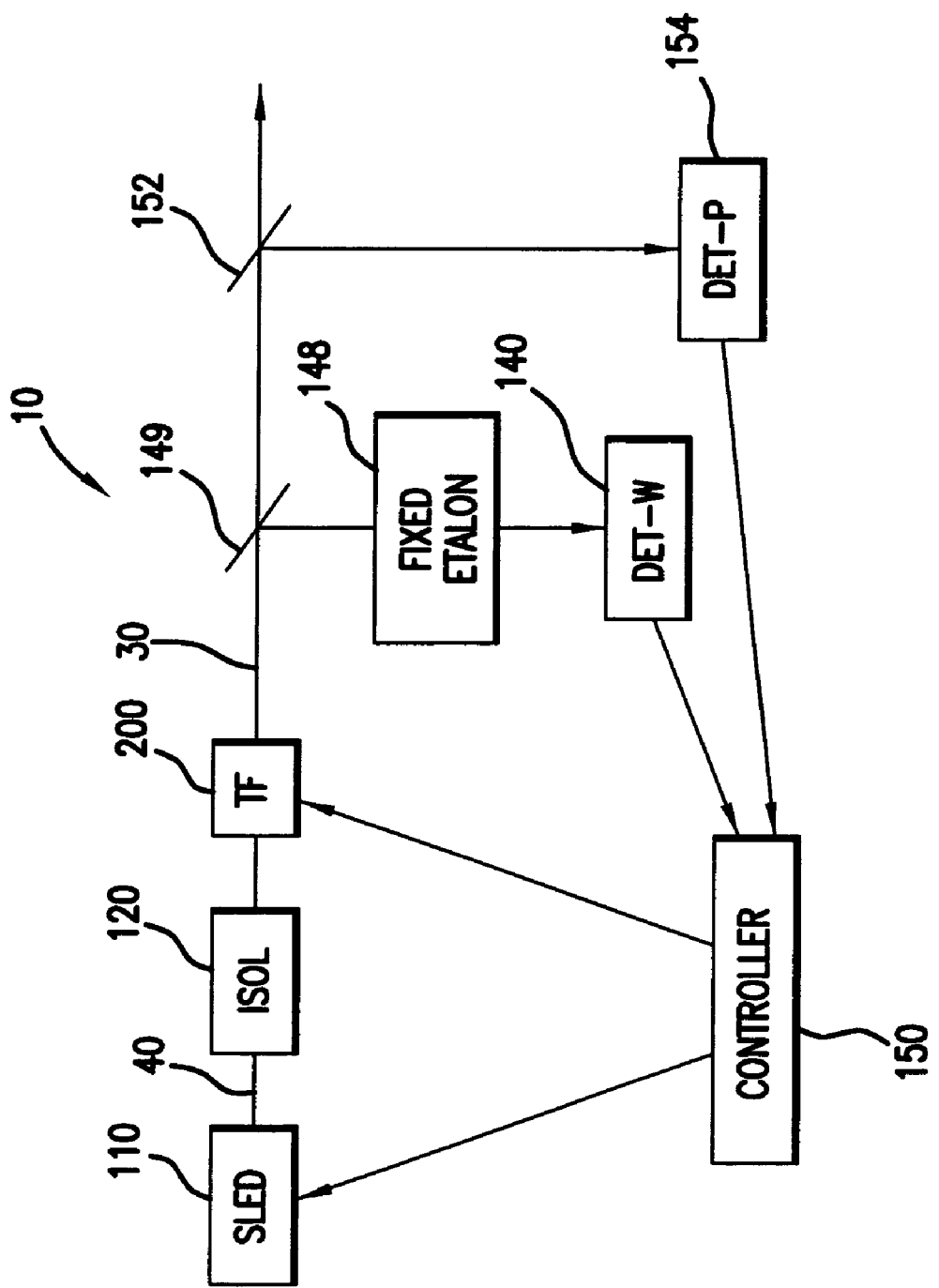
FIG. 6 is a block diagram of an embodiment of the tunable source with both a wavelength and power reference detector.

FIG. 6 illustrates the general operation provided by a controller 150 of the tunable source 10. Specifically, the controller 150 is used to control the power or current supplied to the SLED chip 110. Its broadband signal 40 is coupled to the isolator 120. The controller also controls the tunable pass band of the tunable filter system 200 to generate the tunable signal 30.

In the case of monitoring the frequency of the tunable signal, a first tap 149 couples a portion of the tunable signal to a spectral reference 148, which in the illustrated embodiment, is a fixed etalon. This allows the detector 140 to detect the wavelength of the tunable signal 30 during the scan.

In the preferred embodiment, a power detector 154 is also provided. This is added to the optical train using second tap 152, which again couples the portion of the tunable signal 30 to a power detector 154. The controller 150 controls and monitors the wavelength detector 140 and the power detector 154 to determine both the wavelength and the power in the tunable signal 30.

Figure 7:
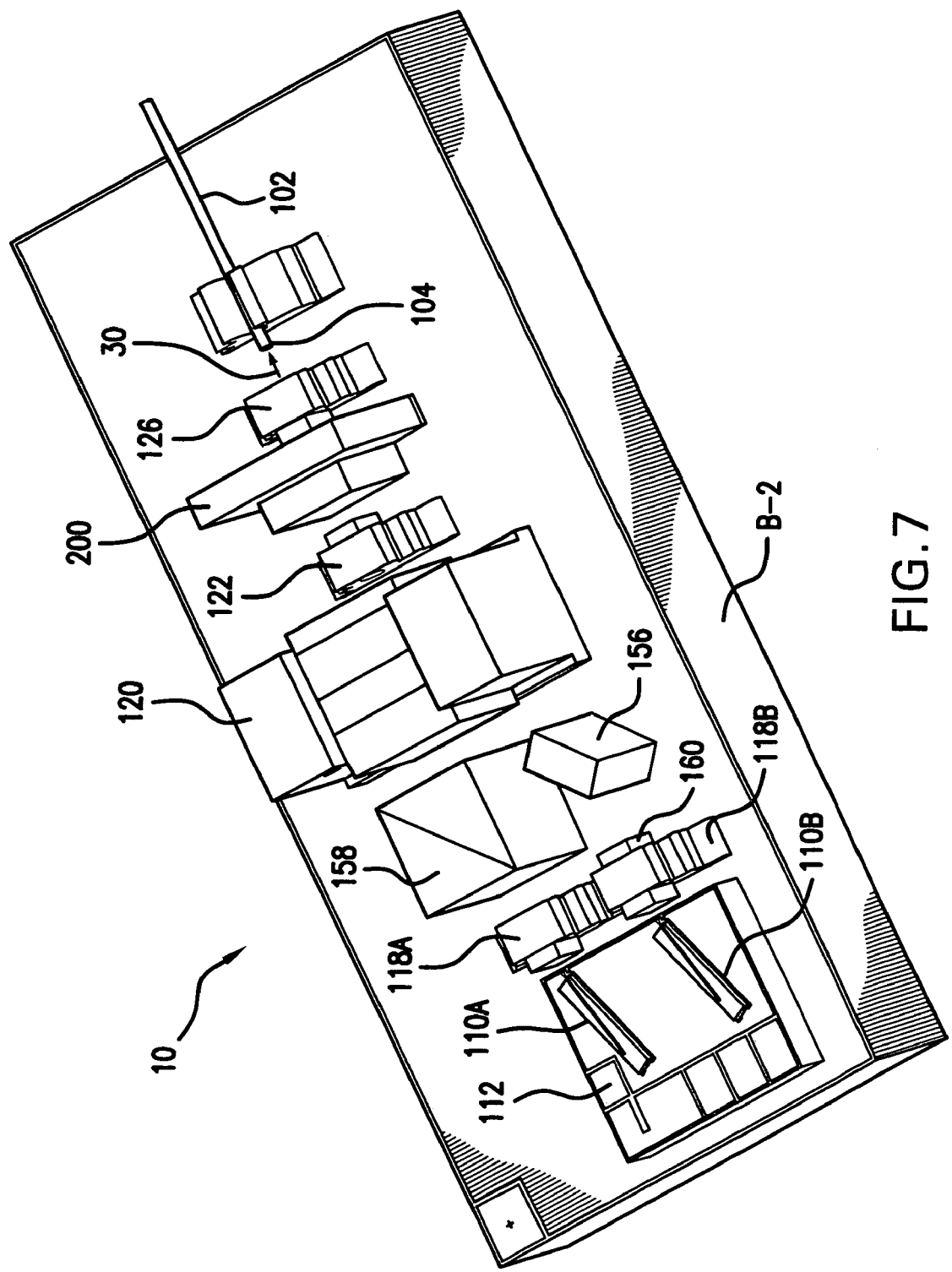
FIG. 7 is a perspective view showing still another embodiment of a tunable source, according to the present invention, using two SLED chips.

FIG. 7 illustrates another embodiment of the tunable source 10. This embodiment is used either to increase the power or the spectral width of the scan band of the tunable source 10. Specifically, multiple SLED chips, and specifically two SLED chips 110A and 110B, are installed together on the optical bench B-2. In the illustrated embodiment, the SLED chips 110A and 110B are installed on a common sub-mount 112, which is in turn, bonded to the bench B-2.

Two first lens components 118A, 118B are provided to couple the broadband signals from their respective SLED chips 110A, 110B and collimate those beams. A combination of a fold mirror 156 and a combiner 158 are provided to combine the broadband signals from each of these SLED chips 110A, 110B into a single broadband signal, which is coupled through the isolator 120.

The beam from the isolator 120 is then focused by a second lens component 122 into the tunable filter 200. A third lens component 126 then couples the tunable signal into the optical fiber 102 via the endface 104.

In the high power version of the FIG. 7 embodiment, a polarization rotator, such as a quarterwave plate 160 is provided in the beam path of one of the SLED chips 110A, 110B. In the illustrated embodiment, this polarization rotator 160 is provided in the beam path of the second SLED chip 110. This rotates the polarization of the light from the second SLED chip 110B by 90°. Then, the combiner 158 is a polarization combiner that is transmissive to the polarization of the light from the first SLED chip 110A, but reflective to the polarization of light from the second SLED chip 110B.

As a result, the beams from each of the SLED chips 110A, 110B are merged into a common broadband signal with increased power.

In a second implementation of the FIG. 7 embodiment, the SLED chips 110A, 110B operate at different spectral bands. Specifically, SLED chip 110A generates light in a scan band A and SLED chip 110B generates light in an adjacent but different scan band B. The combiner 158 is a wavelength division multiplex combiner that is configured to be transmissive to the band of light generated by the SLED chip 110A, but reflective to light in the band generated by SLED chip 110B. As a result, the combined signal generated together by the SLED chip 110A, 110B has a broader scanband then could be generated by each of the SLED chips individually. This allows for increased bandwidth in the tunable signal 30 that is generated by the tunable source 10.

Figure 8:
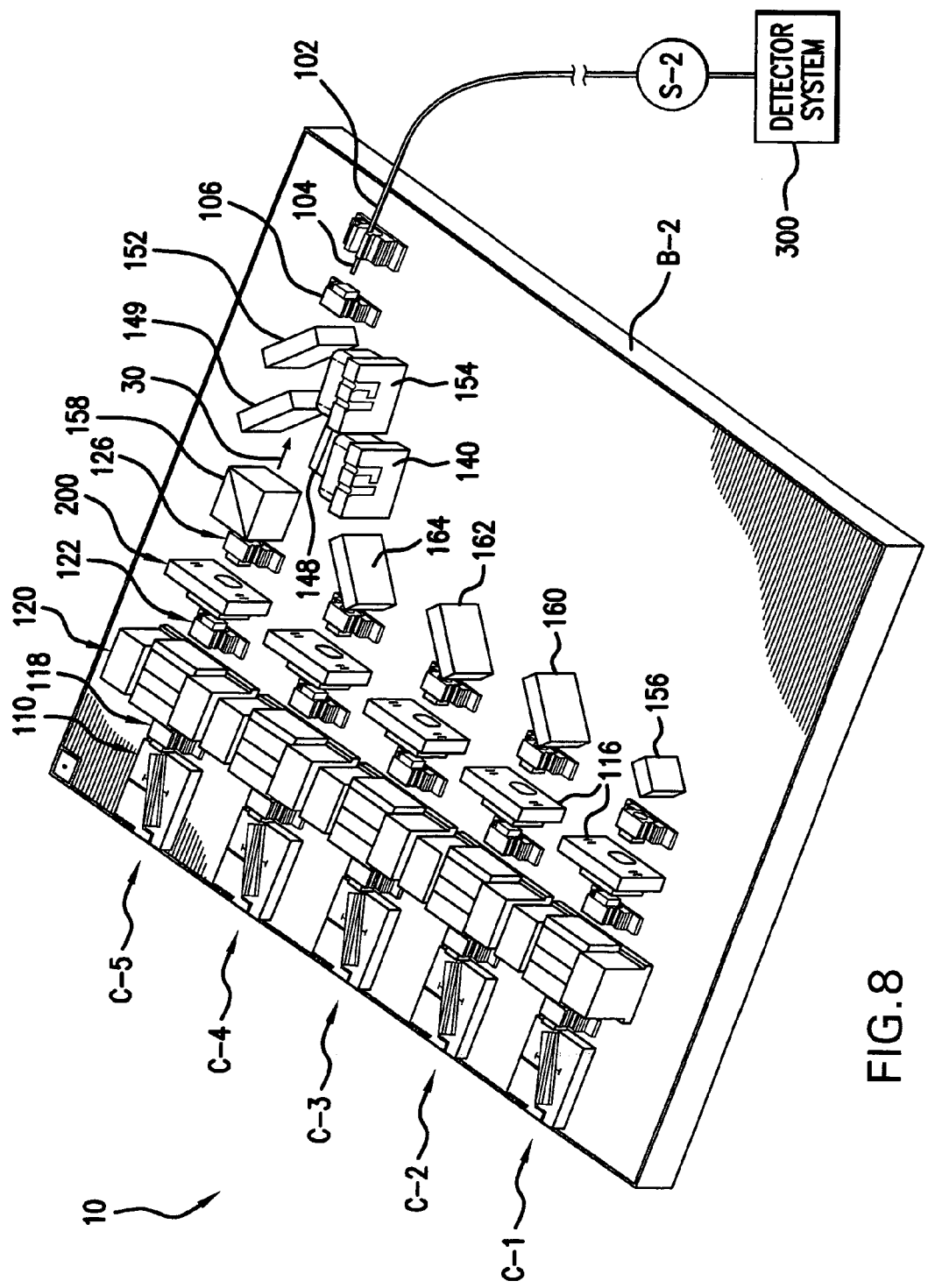
FIG. 8 is a perspective view showing a further embodiment of a tunable source, according to the present invention using multiple SLED chips and tunable filters.

FIG. 8 illustrates another embodiment of the tunable source 10. This embodiment uses a tunable filter system 200, which includes an array of tunable filters 116 and broadband light sources in order to increase the spectral width of the scanband. Typically, and in the illustrated embodiment, an array of five SLED chips 110 are mounted in common on the bench B-2. The light from each of these SLED chips 110 is collimated by respective first lens components 118. Specifically, there is a separate lens component 118 for each of these SLED chips 110. Separate isolators 120 are then provided for the broadband signals from each of the SLED chips 110.

An array of second lens components 122 is further provided to couple the broadband signal into an array of tunable filters 200. Specifically, separate Fabry-Perot tunable filters 116 are used to filter the signal from each of the respective SLED chips 110. Finally, an array of third lens components 126 is used to re-collimate the beam from the tunable Fabry-Perot filters 116 of the tunable filter system 200.

For channel 1, C-1, a fold mirror 156 is used to redirect the beam from the SLED chip 110. The WDM filter 160 is used to combine the broadband signal from the SLED chip 110 of channel C-2 with the signal from channel C-1. Specifically, the filter 160 is reflective to the wavelength range generated by the SLED chip 110 of channel C-2, but transmissive to the wavelength range of light generated by the SLED chip 110 of channel C-1.

In a similar vein, WDM filter 162 is reflective to the signal band generated by the SLED chip 110 of channel C-3, but transmissive to the bands generated by SLED chips 110 of channels C-1 and C-2. WDM filter 164 is reflective to the light generated by SLED chip 110 of channel C-4, but transmissive to the bands generated by the SLED chips 110 of channels C-1, C-2, and C-3. Finally, WDM filter 158 is reflective to all of the SLED chips, but the SLED chip 110 of channel C-5. As a result, the light from the array of SLED chips is combined into a single broad band tunable signal 30.

A first tap 149 is provided to reflect a portion of the light through the etalon 148 to be detected by the wavelength detector 140. Then, another portion is reflected by tap 152 to the power detector 154. The remaining tunable signal is coupled by the fourth lens component 106 into the optical fiber 102 via the endface 104.

The FIG. 8 embodiment can operate according to a number of different modes via a controller 150. Specifically, in one example, only one of the SLED chips in channels C-1 to C-5 is operating at any given moment in time. As a result, the tunable signal 30 has only a single spectral peak. The full scan band is achieved by sequentially energizing the SLED chip of each channel C-1 to C-5. This tunable signal is scanned over the entire scan band covered by the SLED chips of channels C-1 to C-5 turning on the SLED chips in series, or sequentially.

In another mode, each of the SLED chips is operated simultaneously. As a result, the tunable signal has spectral peaks in each of the scan bands, covered by each of the SLED chips 110 simultaneously. This system results in a more complex detector system 300, which must demultiplex the separate scan bands from each of the SLED chips 110 from each of the channels at the detector. Specifically, in one embodiment, five (5) detectors are used with a front-end wavelength demultiplexor.

Figure 9:
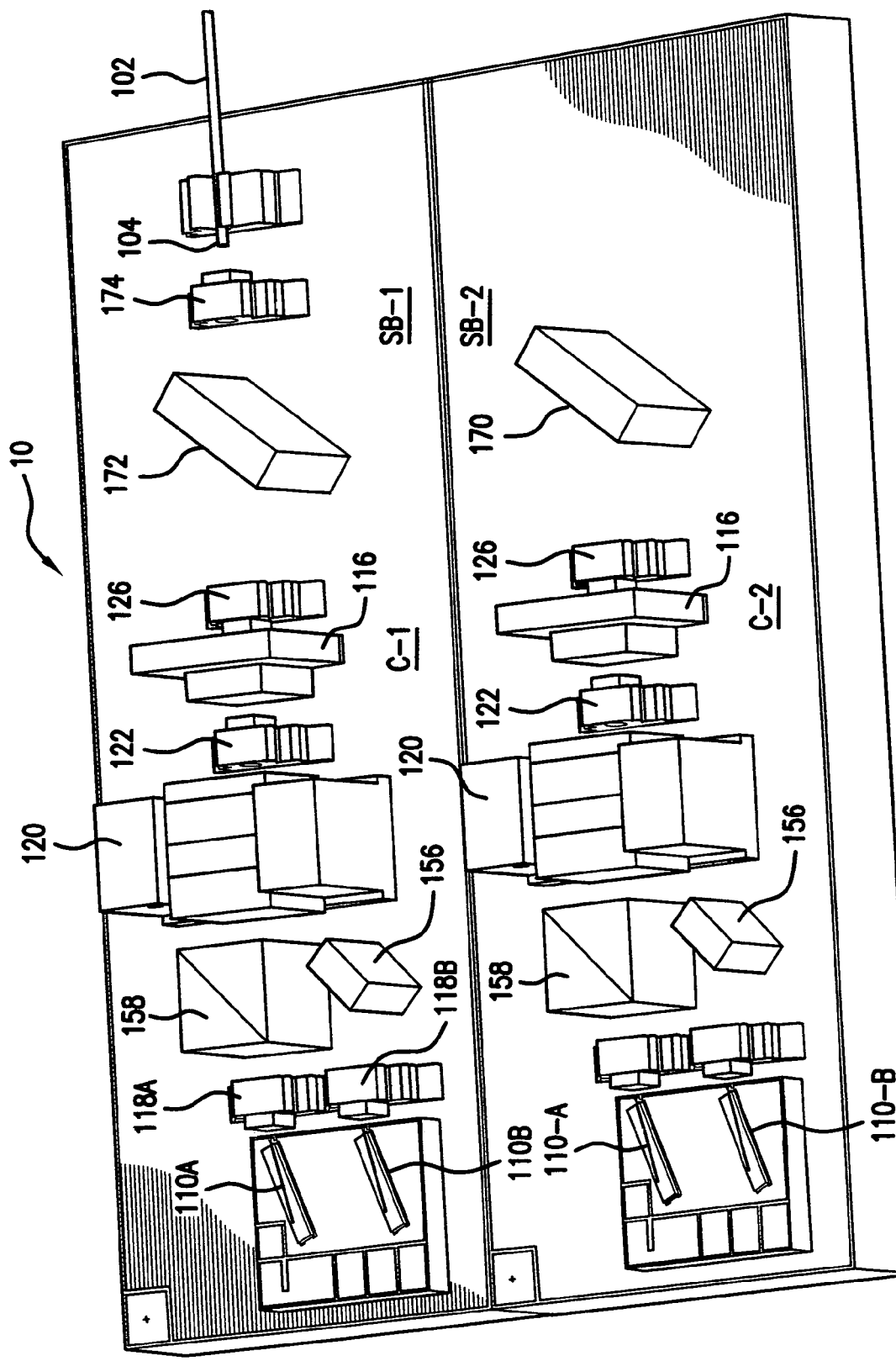
FIG. 9 is a perspective view showing another embodiment of a tunable source, according to the present invention, using parallel filters and multiple SLED sources.

FIG. 9 shows an embodiment of the tunable source 10 that has both increased power and increased scanning range over a single SLED. It comprises two subcomponents, which are configured as illustrated in FIG. 7 embodiment. Specifically, each channel C-1, C-2 has two SLED chips 110A, 110B that are polarization combined. The output is isolated by an isolator 120 and then filtered by a tunable filter 116 for each channel C-1, C-2. The signals from the two channels are then wavelength multiplexed using a combination of a fold mirror 170 and a dichroic or WDM filter 172. Specifically, the dichroic mirror 172 is transmissive to the scan band of the SLED chips 110A, 110B of channel C-1, but reflective to the SLED chips 110A, 110B of channel C-2.

In order to improve the manufacturing yield of the FIG. 9 embodiment, in one implementation, each of the channels C-1 and C-2 are fabricated on separate sub-benches SB-1 and SB-2. The sub-benches SB-1, SB-2 are then bonded to each other or to a common bench in order to yield the FIG. 9 embodiment.

Figure 10:
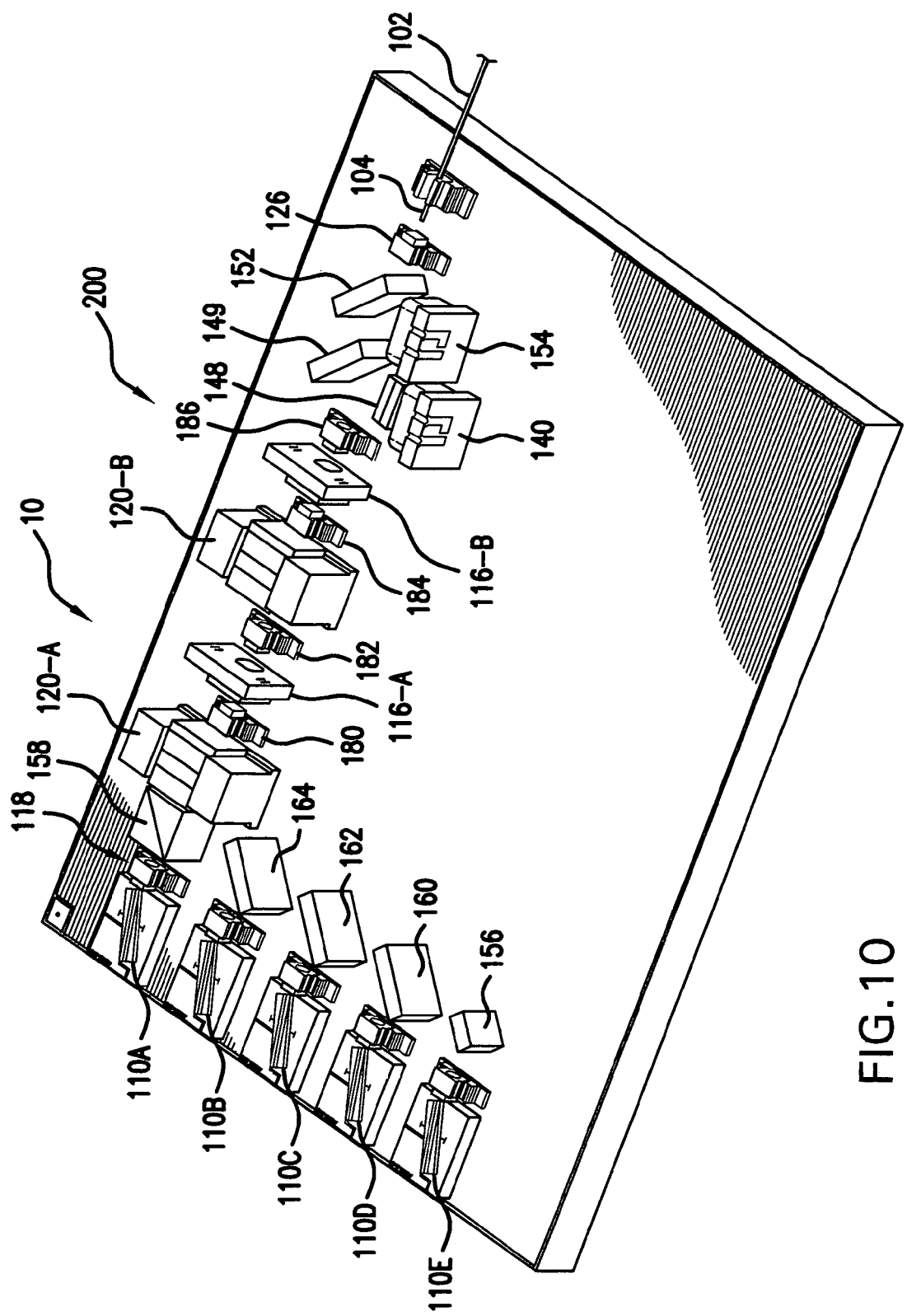
FIG. 10 is a perspective view showing a further embodiment of a tunable source, according to the present invention, using serial filters.

FIG. 10 illustrates still another embodiment, which covers a wide spectral band. Specifically, it includes five SLED chips 110A to 110E. A series of first lens optical components 118 are used to collimate the beams from each of the SLED chips 110A–110E. In the present embodiment, the SLED chips 110A to 110E, each operate over different spectral bands. They are then wavelength combined using a combination of fold mirrors and filters 156, 160, 162, 164 and 158, as discussed with reference to the FIG. 8 embodiment.

The FIG. 10 embodiment further includes, preferably, two isolators 120A, 120B. These isolate respective tunable filters 116A, 116B. Lens components 180, 182, 184, and 186 are used to couple the optical signal generated by the SLEDS 110A–110E, through the first tunable filter 116A and the second tunable filter 116B of the tunable filter system 200, and then, through the wavelength tap 149 and the power tap 152 to the endface 104 of the optical fiber 102.

Figure 11:
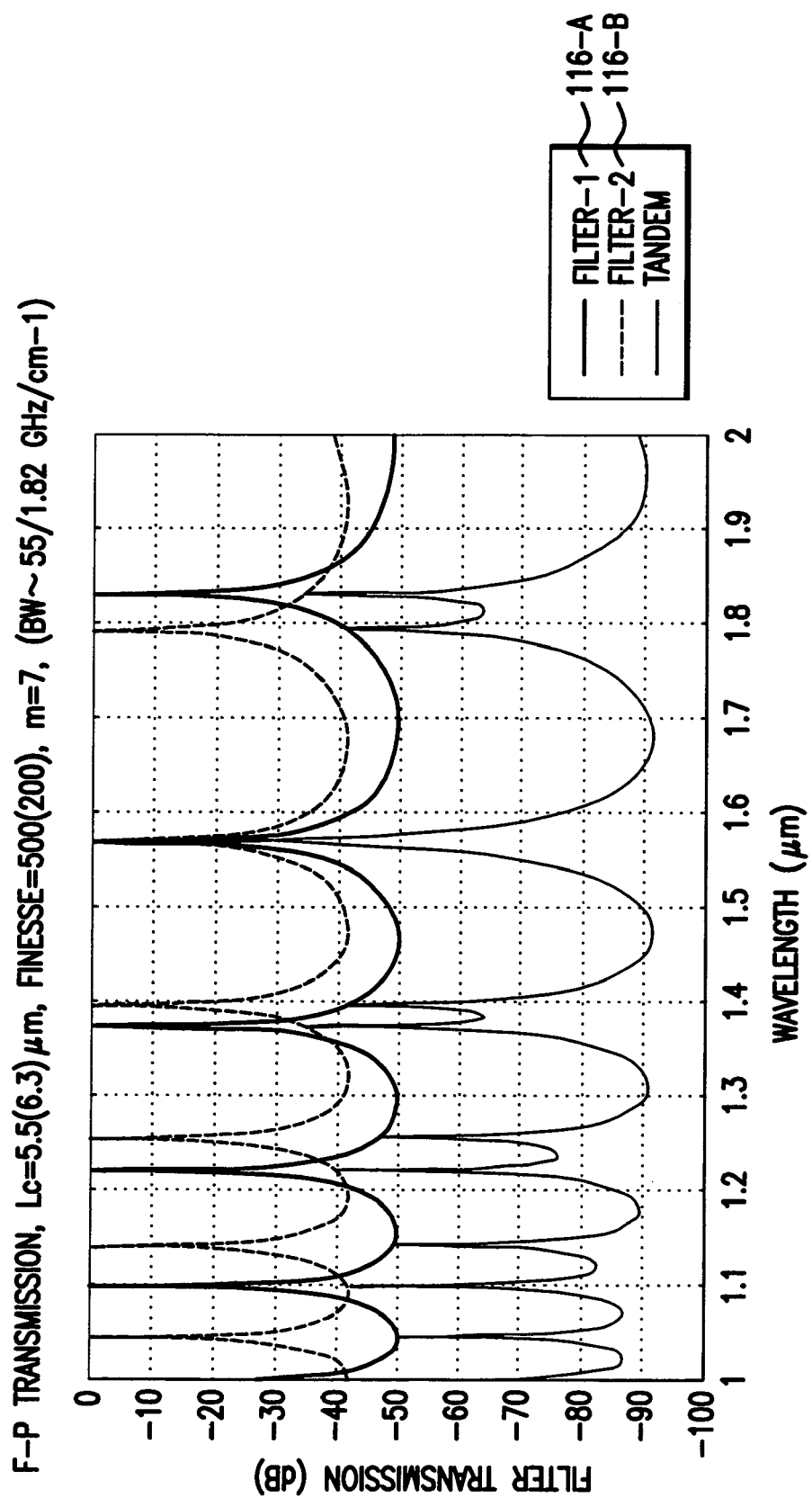
FIG. 11 is a plot of wavelength as a function of transmission showing the relationship between the free spectral ranges of the serial filters, in one embodiment.

The use of the five SLED chips 110 increases the effective scan band of the tunable source 10. In the preferred embodiment, the tandem tunable filters have free spectral ranges FSR as illustrated in FIG. 11.

Specifically, filter 1 116A, and filter 2 116B have different free spectral ranges. As a result, they function in a vernier configuration. This addresses limitations in the free spectral range of the tunable filters individually.

Typically, if a single tunable filter was used, its free spectral range would have to be at least as wide as the total scan band of the broad band signals generated by the sources. In the illustrated embodiment, the tunable filters are combined to increase the free spectral range of the tunable filter system, since the peak transmissivity, through both tunable filters 116A–116B, only arises at wavelengths where the passbands of the two filters 116A–166B are coincident.

Figure 12A:
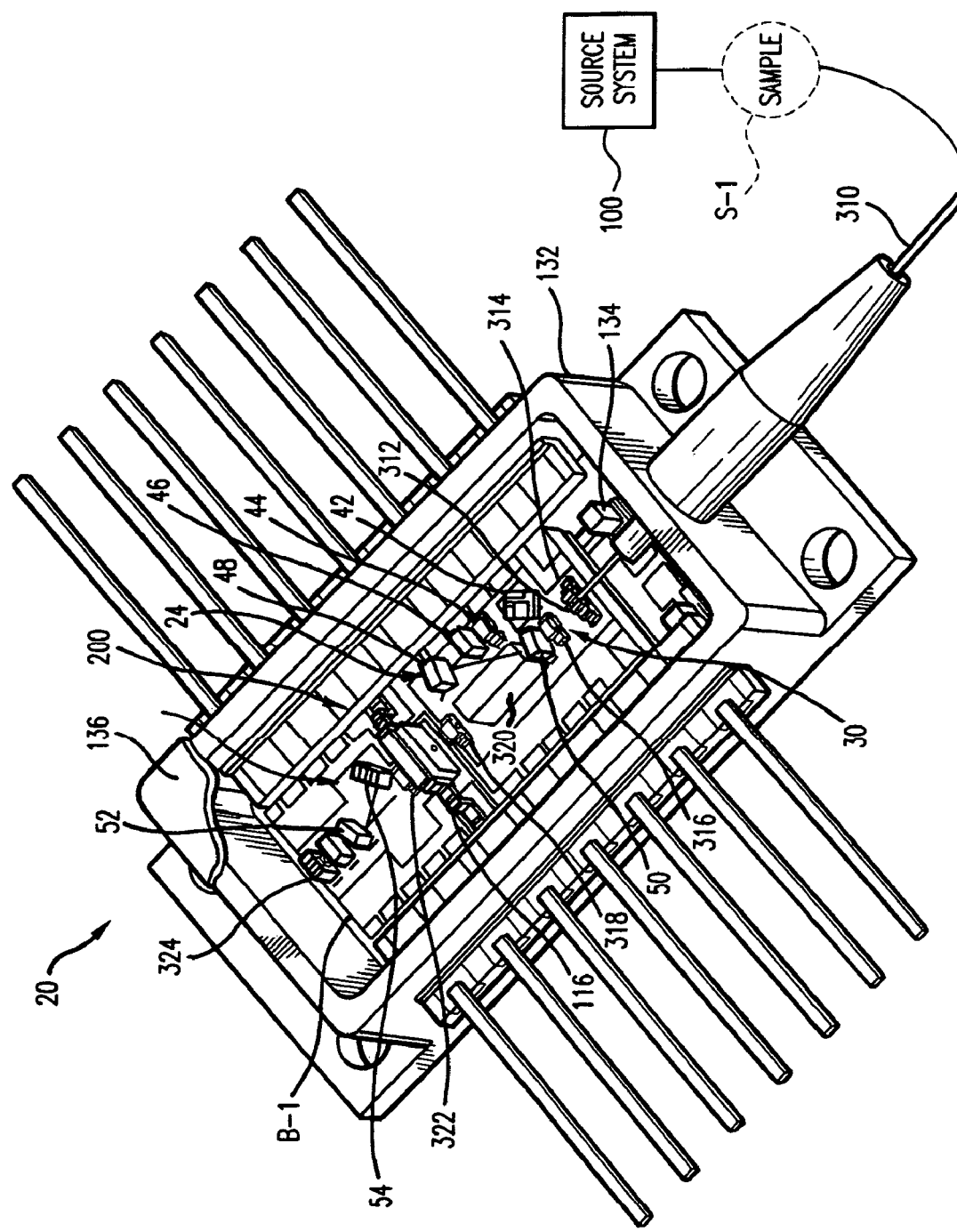
FIG. 12A is a perspective view of a tunable detector spectroscopy system, according to the present invention.
Figure 12B:
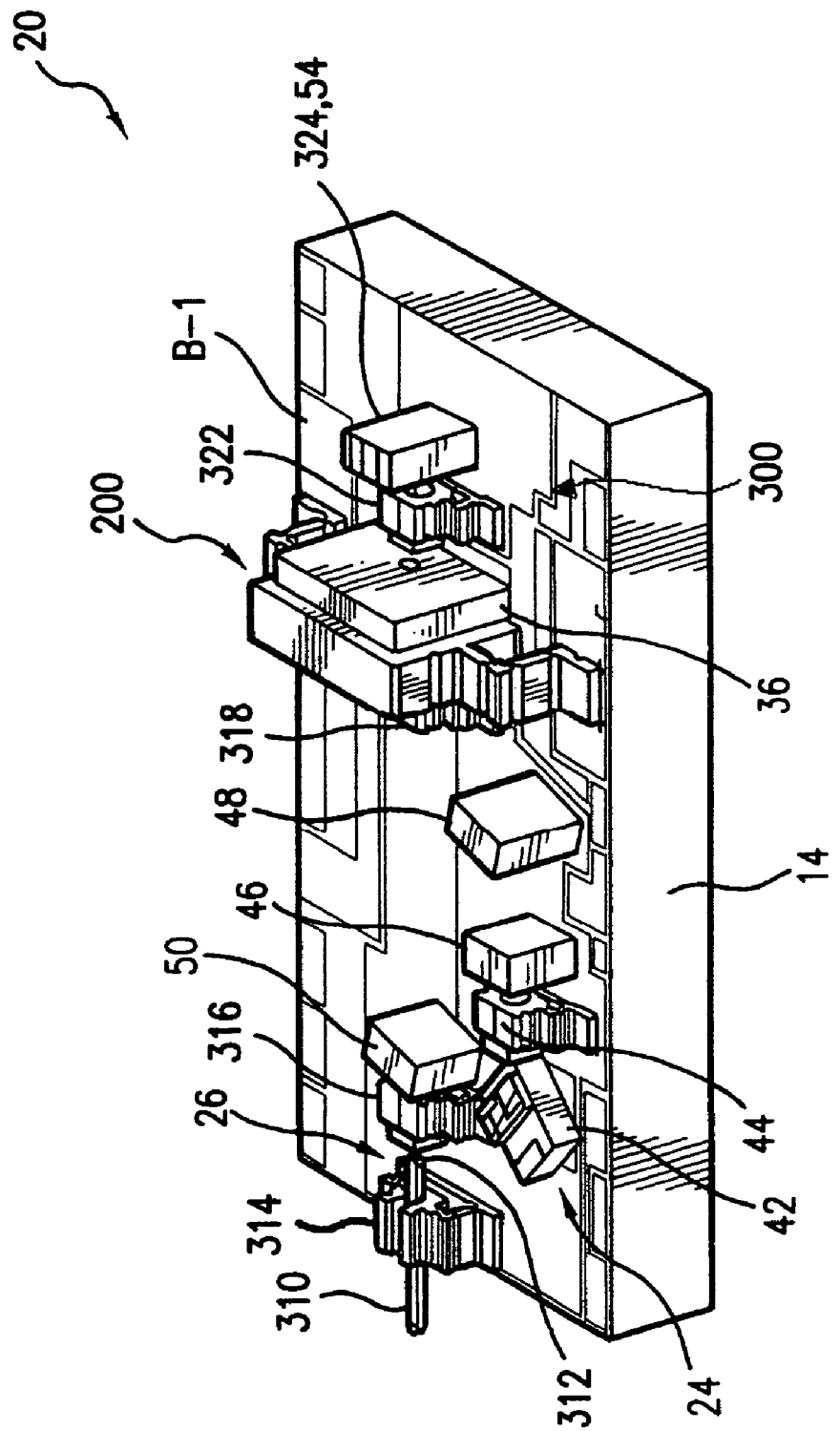
FIG. 12B is a perspective view of another embodiment of a tunable detector spectroscopy system, according to the present invention.

FIGS. 12A and 12B show tunable detector systems 20, to which the principles of the present invention are also applicable.

Specifically, with reference to FIG. 12A, the tunable detector system generally comprises a package 132 and an optical bench B-1, which is sometimes referred to as a submount. The bench B-1 is installed in the package 132, and specifically on a thermoelectric (TE) cooler 134, which is located between the bench B-1 and the package 132, in the specific illustrated embodiment.

The package 132, in this illustrated example, is a butterfly package. The package's lid 136 is shown cut-away in the illustration.

The tunable detector optical system, which is installed on the top surface of the bench B-1, generally comprises the detector system 300, the tunable filter system 200, and an optional reference source system 24.

In more detail, the optical signal from the target S—I to be monitored is transmitted to the system via a fiber pigtail 310, in the illustrated example. This pigtail 310 terminates at an endface 312 that is secured above the bench B-1 using a fiber mounting structure 314 in the illustrated implementation. The optical signal passes through a first lens optical component 316, which collimates the beam to pass through an isolator 320. A second lens optical component 318 launches the optical signal into the tunable filter system 200. A MEMS implementation of the tunable filter is shown. The filtered signal passes through a third lens optical component 322 and is then detected by an optical signal detector 324.

In the illustrated implementation, each of the lens and tunable filter optical components comprises the optical element and a mounting structure that is used to secure the optical element to the bench, while enabling most installation alignment.

Turning to the path of the optical reference, the emission from a reference light source 42, such as a broadband source, e.g., a SLED, passes through reference lens optical component 44 to a fixed filter 46, which, in the present implementation, is a fixed etalon. It converts the broadband spectrum of the SLED 42 into a series of spectral peaks, corresponding to the various orders of the etalon transmission, thereby producing the stable spectral features of the optical reference.

The optical reference is then reflected by fold mirror 48 to a dichroic or WDM filter 50, which is tuned to be reflective at the wavelength of the optical reference, but transmissive within the band of the optical signal. Thus, the optical reference is similarly directed to the optical filter system 200.

At the detector system 20, a dichroic filter 52 reflects the optical reference to a reference detector 54.

FIG. 12B shows an operationally similar tunable optical filter system 20 for the purposes of the present invention. Reference numerals have been used for functionally equivalent parts. The differential between the two designs lies in the design of the detector system 300. This second embodiment utilizes only a single detector 324, 54 that detects both the optical reference and the optical signal. In this illustration, the package is not shown for clarity.

Figure 13:
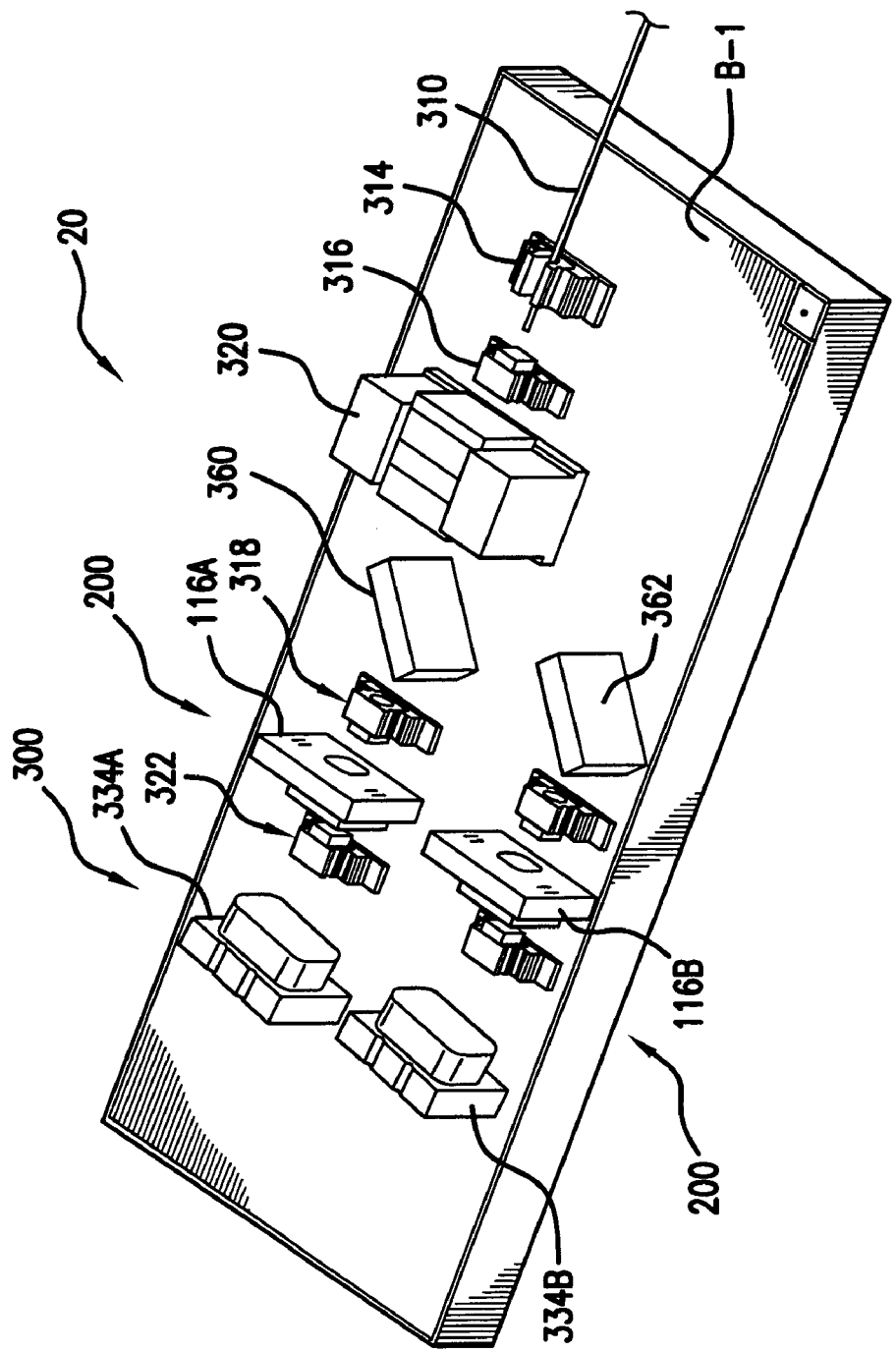
FIG. 13 is a perspective view of still another embodiment of a tunable detector spectroscopy system, according to the present invention, using multiple parallel filters.

FIG. 13 shows another embodiment of the tunable detector 20. The signal from the target is transmitted to the detector 20 via fiber 310. A first lens component 316 collimates the light from the fiber. Second lens components 318 couple the light into the tunable filters 116A, 116B of the filter system 200. Third lens components 322 focus the light to the detector system 300.

This version uses two tunable filters 116A, 1116B, each filtering a portion of the scan band. Corresponding detectors 334A, 334B detect the transmitted signal from each filter.

The spectrum is divided into two subbands by WDM filter 360, which reflects half of the spectral scan band to the second filter 116B via fold mirror 362. The other half of the spectrum is transmitted through the WDM filter 360 to tunable filter 116A.

Figure 14:
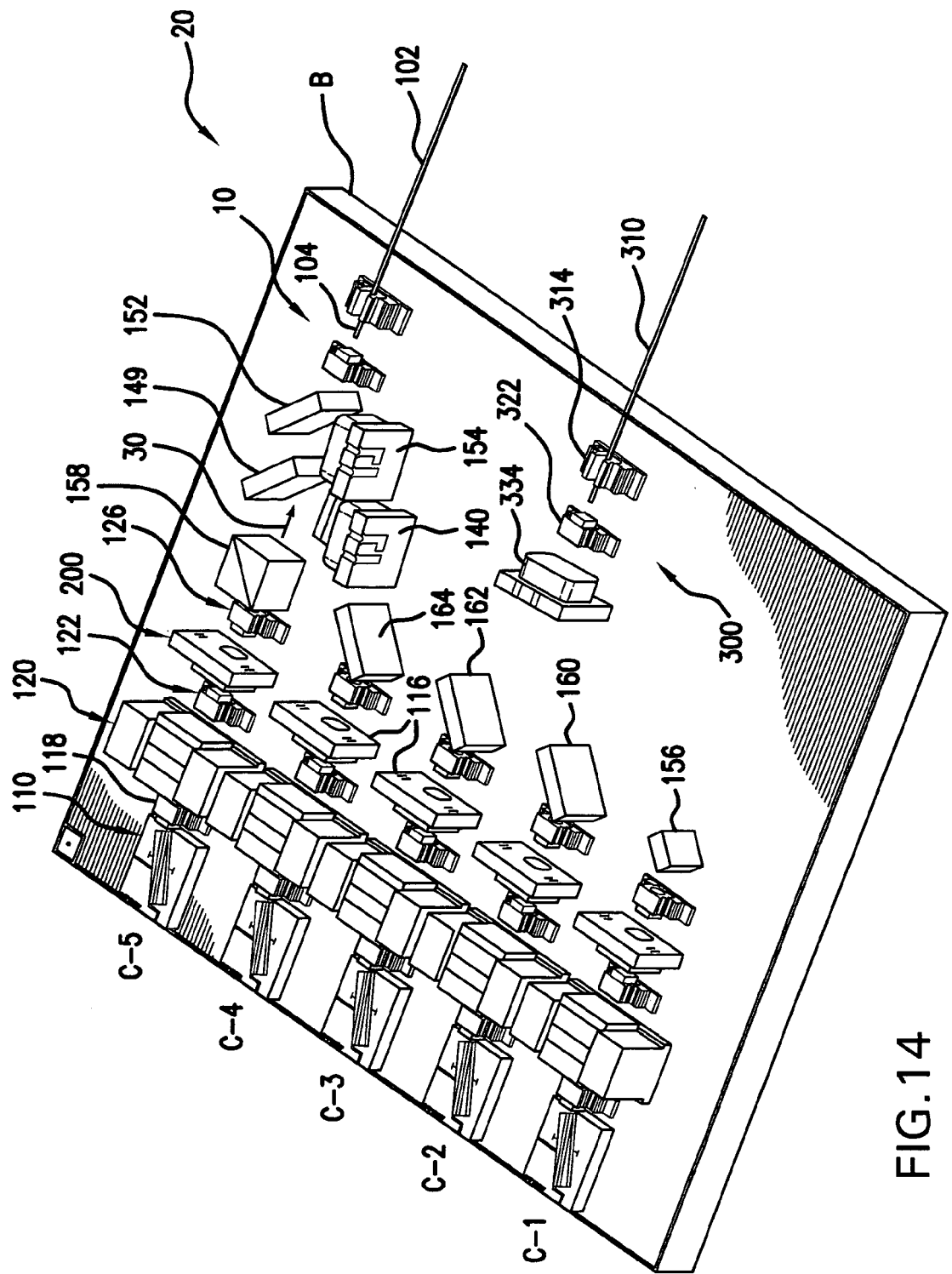
FIGS. 14 and 15 show two fully integrated spectroscopy systems in which a tunable source and a detector system are integrated on the same bench.

FIG. 14 shows a single bench fully integrated system according to still another embodiment. It generally operates as described relative to the FIG. 8 embodiment. Specifically, it uses a series of SLEDs in five channels, yielding a tunable source 10, to generate a wide band tunable signal 30. The detector system 300 is integrated on the same bench B and the tunable source. Specifically, light returning from the target in fiber 310 is coupled to detector 334 using lens component 322.

Figure 15:
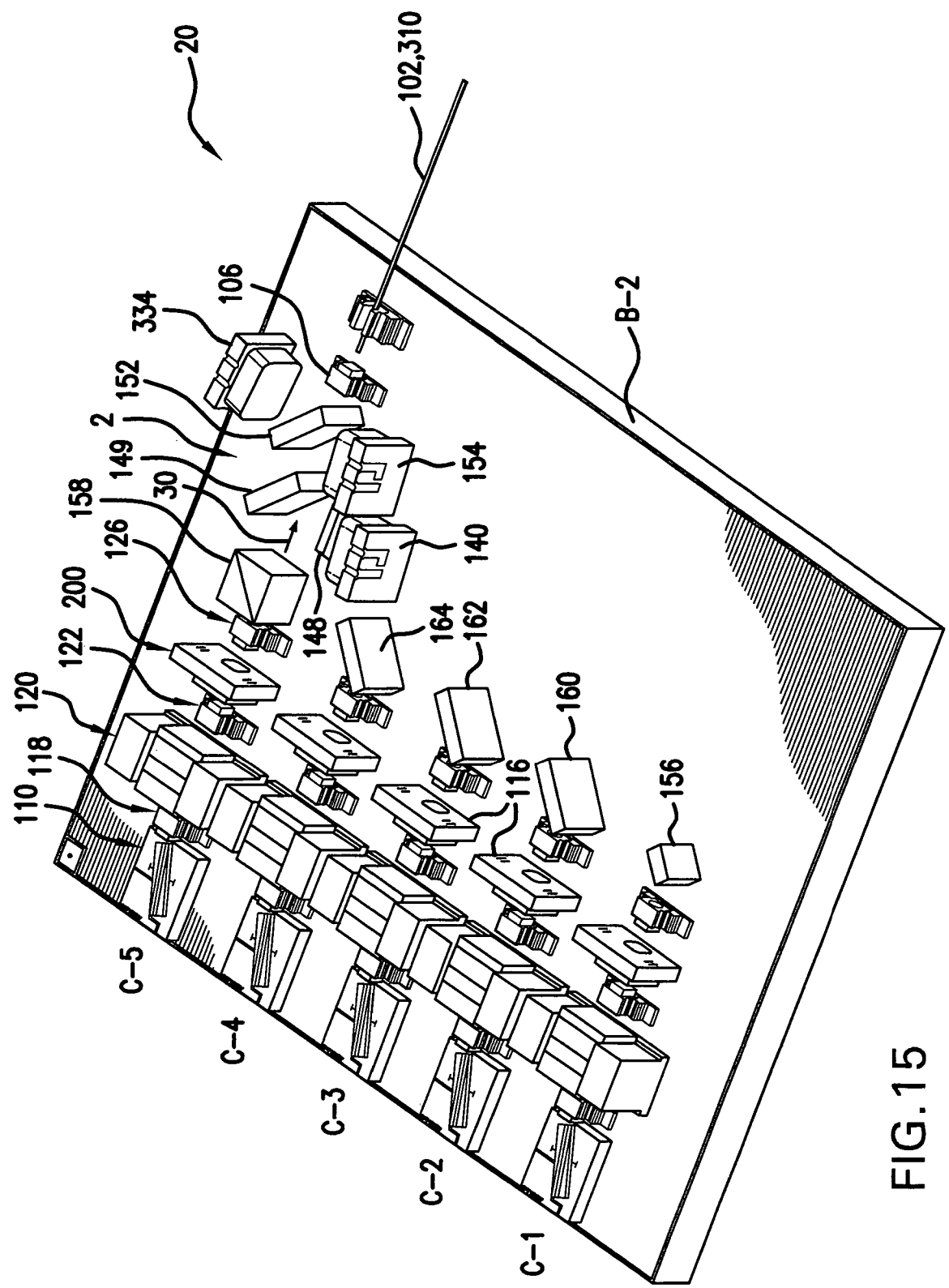

FIG. 15 shows another single bench fully integrated system according to still another embodiment. Here, the light to and from the target is carried in the same fiber 102, 310. The tap substrate 152 is used to direct outgoing light 30 to the power detector 154 and light returning from the target to the detector 334.

While this invention has been particularly shown and described with references to preferred embodiments thereof, it will be understood by those skilled in the art that various changes in form and details may be made therein without departing from the scope of the invention encompassed by the appended claims.

What is claimed is:

1. A spectroscopy system, comprising:
   a source system for generating light to illuminate a sample over a broadband;
   a tunable Fabry-Perot filter system for spectrally filtering the light generated by the source system to generate a tunable signal to irradiate the sample;
   a tap for diverting a portion of the signal from the Fabry Perot tunable filter to a detector; and
   a detector system for detecting the light filtered by the tunable Fabry-Perot filter from the sample,
   wherein at least two of the source system, tunable Fabry-Perot filter system, and the detector system are integrated together.

2. A spectroscopy system as claimed in claim 1, wherein the source system comprises a semiconductor diode source.

3. A spectroscopy system as claimed in claim 1, wherein the source system comprises multiple, multiplexed diode chips, operating at different wavelength ranges.

4. A spectroscopy system as claimed in claim 1, wherein the source system comprises at least one superluminescent light emitting diode (SLED) source.

5. A spectroscopy system as claimed in claim 1, wherein the tunable Fabry-Perot filter system comprises multiple, parallel filters.

6. A spectroscopy system as claimed in claim 1, wherein the tunable Fabry-Perot filter system comprises multiple filters for filtering different wavelength ranges.

7. A spectroscopy system, comprising:
   a source system for generating light to illuminate a sample;
   a tunable Fabry-Perot filter system for filtering the light generated by the source; and
   a detector system for detecting the light filtered by the tunable Fabry-Perot filter from the sample,
   wherein at least two of the source system, tunable Fabry-Perot filter system, and the detector system are integrated together; and wherein the tunable Fabry-Perot filter system comprises multiple, serial filters.

8. A spectroscopy system as claimed in claim 7, wherein the multiple, serial filters have different free spectral ranges.

9. A spectroscopy system as claimed in claim 1, wherein the detector system comprises multiple detectors responsive to different wavelength ranges.

10. A spectroscopy system as claimed in claim 1, wherein the source system and the Fabry-Perot filter system are integrated on a common bench, in a common package.

11. A spectroscopy system as claimed in claim 1, wherein the Fabry-Perot filter system and the detector system are integrated on a common bench, in a common package.

12. A spectroscopy system as claimed in claim 1, wherein the source system, Fabry-Perot filter system, and the detector system are integrated on a common bench, in a common package.

13. A spectroscopy system as claimed in claim 1, wherein the Fabry-Perot filter system comprises at least one MEMS tunable filter.

14. A spectroscopy system as claimed in claim 1, further comprising an isolation system between the source system and the tunable Fabry-Perot system for preventing backreflections in to the source system.

15. A spectroscopy system as claimed in claim 1, wherein:
the source system comprises a broadband source for generating broadband light.

16. A spectroscopy system as claimed in claim 15, wherein the broadband source comprises a light emitting diode.

17. A spectroscopy system as claimed in claim 15, wherein the broadband source comprises a superluminescent light emitting diode.

18. A spectroscopy system as claimed in claim 15, wherein the broadband source comprises an array of diodes.

19. A spectroscopy system as claimed in claim 1, wherein the source system and the Fabry Perot filter system are installed in common on an optical bench.

20. A spectroscopy system as claimed in claim 1, further comprising a stable spectral reference interposed between the detector and the tap.

21. A spectroscopy system as claimed in claim 20, wherein the reference is a gas cell.

22. A spectroscopy system as claimed in claim 20, wherein the reference is an etalon.

23. A spectroscopy system, comprising:
a source system for generating light to illuminate a sample over a broadband;
a tunable Fabry-Perot filter system for spectrally filtering the light generated by the source to generate a tunable signal to irradiate the sample;
a detector system for detecting the light filtered by the tunable Fabry-Perot filter from the sample;
a controller for modulating the source system;
a detector for detecting the tunable signal from the Fabry Perot filter; and
a lock-in amplifier responsive to the controller for locking onto a modulation of the tunable signal;
wherein at least two of the source system, tunable Fabry-Perot filter system, and the detector system are integrated together.

24. A spectroscopy system as claimed in claim 1, wherein the tunable Fabry-Perot filter system comprises a MEMS tunable movable mirror die and a fixed mirror substrate, which is bonded to the MEMS mirror die, wherein the filter is edge bonded onto an optical bench.

25. A spectroscopy system as claimed in claim 24, wherein the fixed mirror substrate extends below a bottom of the MEMS mirror die for attachment to the optical bench.

26. A spectroscopy system as claimed in claim 24, wherein the MEMS mirror die is separated from the optical bench and supported by the fixed mirror substrate.

27. A spectroscopy system, comprising:
a semiconductor source system for generating light to illuminate a sample;
a tunable Fabry-Perot filter system for filtering the light generated by the source; and
a detector system for detecting the light filtered by the tunable Fabry-Perot filter from the sample;
an optical bench to which the semiconductor source system and the tunable Fabry-Perot filter system are attached;
a hermetic package containing the optical bench;
a temperature controller for stabilizing a temperature of the semiconductor source system and the tunable Fabry-Perot filter system in the hermetic package.

* * * * *